United States Patent [19]

Cocozza

[11] Patent Number: 4,884,565

[45] Date of Patent: Dec. 5, 1989

[54] INSUFFLATOR FOR THE ADMINISTRATION OF DRUGS IN THE FORM OF A POWDER PRE-DOSED INTO OPERCOLA

[75] Inventor: Salvatore Cocozza, Milan, Italy

[73] Assignee: Miat S.p.A., Milan, Italy

[21] Appl. No.: 224,816

[22] Filed: Jul. 27, 1988

[30] Foreign Application Priority Data

Aug. 17, 1987 [IT] Italy ............................... 21668 A/87

[51] Int. Cl.⁴ .............................................. A61M 15/00
[52] U.S. Cl. ............................ 128/203.21; 128/203.15
[58] Field of Search ...................... 128/203.15, 203.21; 604/58; 222/83, 83.5, 85, 86, 87

[56] References Cited

U.S. PATENT DOCUMENTS

| 2,517,482 | 8/1950 | Hall ................................. | 128/203.21 |
| 3,507,277 | 4/1970 | Altounyan et al. .............. | 128/203.21 |
| 3,807,400 | 4/1974 | Cocozza .......................... | 128/203.15 |
| 3,870,046 | 3/1975 | Elliott ............................. | 128/203.15 |
| 3,906,950 | 9/1975 | Cocozza .......................... | 128/203.21 |
| 3,971,377 | 7/1976 | Damani ........................... | 128/203.21 |
| 3,991,761 | 11/1976 | Cocozza .......................... | 128/203.21 |
| 4,013,075 | 3/1977 | Cocozza .......................... | 128/203.15 |
| 4,249,526 | 2/1981 | Dean et al. ...................... | 128/203.15 |
| 4,423,724 | 1/1984 | Young ............................. | 128/203.15 |
| 4,811,731 | 3/1989 | Newell et al. ................... | 128/203.15 |

Primary Examiner—David A. Wiecking
Assistant Examiner—Aaron J. Lewis
Attorney, Agent, or Firm—Ladas & Parry

[57] ABSTRACT

An insufflator for administering pre-dosed powder drugs contained into opercola, which comprises a body having an air-inlet opening and a substantially vertical outlet channel for the air carrying the powder drug, and a device with opposite pins of a known kind for puncturing the operculum, said operculum being placed in a suitable seat. The latter is provided in a member that is turnable relative to said body. Said turnable member can take at least two different positions: a first position, where the operculum can be axially punctured by the above-mentioned opposite, substantially horizontal pins; and a second position, turned 90° relative to said first position, where the opposite holes that have been pierced in the operculum are coaxial with said air-outlet channel.

11 Claims, 3 Drawing Sheets

U.S. Patent  Dec. 5, 1989  Sheet 1 of 3  4,884,565
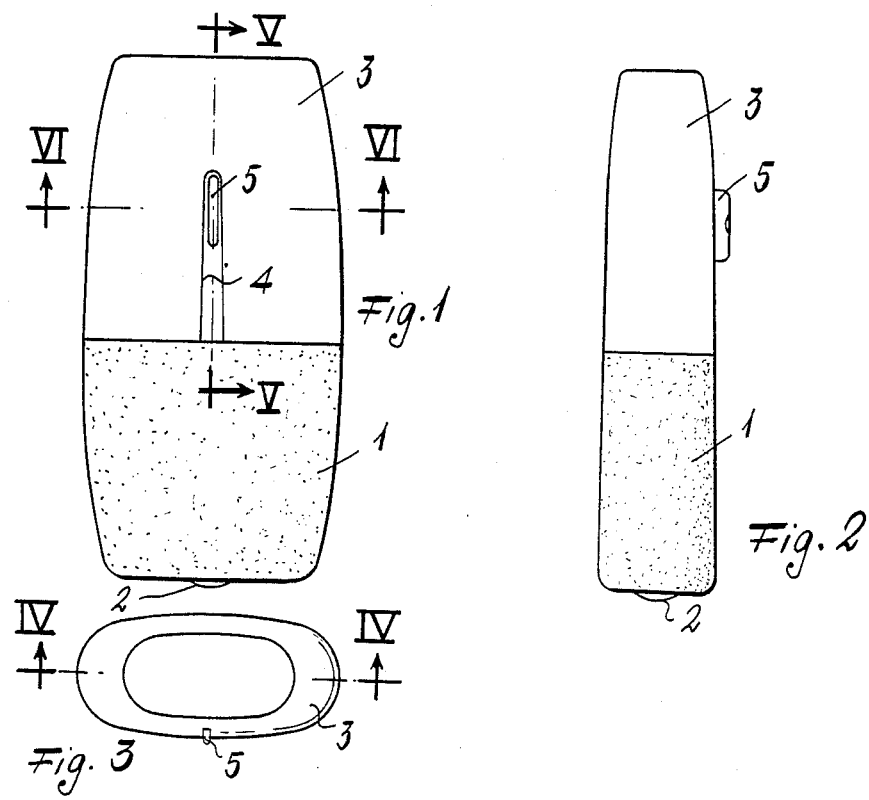
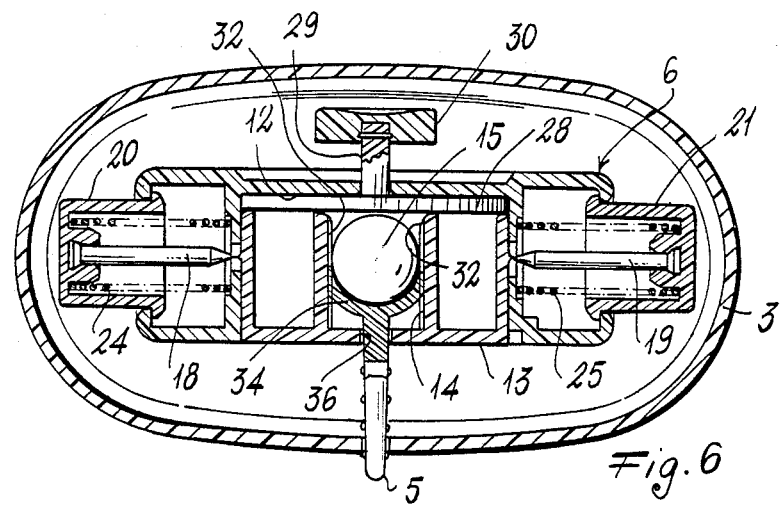

INSUFFLATOR FOR THE ADMINISTRATION OF DRUGS IN THE FORM OF A POWDER PRE-DOSED INTO OPERCOLA

The present invention relates to insufflators for administering drugs which are in the form of finest (micronized) powder pre-dosed into opercula of hard gelatine or other non-toxic material. Said insufflators have a device for puncturing the operculum through which an air stream is then passed that removes the powder from the operculum and acts as an administering vehicle. The air stream is produced by means of a suitable hand-driven pump.

Various kind of insufflators are known in which the operculum containing the drug in the form of a micronized powder which usually takes about ⅓ of the internal volume of the operculum, is placed in a suitable seat provided in the device and is then punctured or otherwise opened for the air stream that is passed through said seat to drag the powder drug.

The above-mentioned puncturing device comprises one or more needles or pins, usually two opposite coaxial pins suitable to pierce in the operculum two corresponding opposite openings for the air stream that flows through said opposite openings to drag the powder contained in the operculum. See for example U.S. Pat. No. 3 906 950 in which the pins are vertically oriented. However, such insufflator, besides being quite complicated, also shows the draw-back that when the operculum is punctured by the two opposite, vertically oriented pins of the puncturing device, due to the combined effect of the gravity force acting onto the powder contained in the operculum and of the drag exerted on the powder by the lower pin when this is drawn out of the operculum, a perceptible amount of powder falls out of the operculum. The action of the air stream, that in this case is produced by a lower hand-pump, is not in the position to completely eject the amount of powder that has fallen from the operculum, thus giving rise to waste of powder drug. Moreover, in the long run, powder piles up especially in the pump, thus giving rise to the need of periodically cleaning the insufflator.

A similar but much simpler insufflator is the one produced by the FISONS LIMITED, England, under the trade mark RINOFLATORE. It comprises a single vertical, upwardly oriented puncturing pin coaxial with the operculum and flow pipe of the air stream. The pin is long enough to actually pierce the operculum from one end to the other. This insufflator shows however the same, or even worse, draw-backs as the former one, concerning the powder coming out of the lower hole and piling up inside the apparatus. This is confirmed by the fact that said insufflator is marketed with a brush included for removing the powder that piles up inside.

A further known apparatus is described in U.S. Pat. No. 4 013 075, and can be used both as an inhaler and as an insufflator. Also in this apparatus the operculum is vertically oriented parallel with the outlet pipe of the air stream. The operculum is opened by cutting its two terminal caps. This apparatus is complicated and expensive to manufacture because it comprises rather elaborated pieces which include two metal blades having a special shape. Moreover, also with this apparatus a perceptible amount of powder is lost at the moment of cutting the two end caps of the operculum.

It is an object of the invention to provide an insufflator for administering drugs in the form of a powder pre-dosed into opercola, which insufflator is simple to manufacture and affords the possibility of utilizing in practice all the powder contained in the opercola.

The above-mentioned objects are achieved by means of the insufflator according to the present invention which comprises a body having an air-inlet opening and a substantially vertical outlet channel for the air carrying the powder drug, and a device with opposite pins of a known kind for puncturing the operculum, said operculum being placed in a suitable seat, characterized in that the seat for the operculum is provided in a member that is turnable relative to said body, and in that said turnable member can take at least two different positions: a first position, or operculum puncturing position, where the operculum can be axially punctured by the opposite, substantially horizontal pins of the above-mentioned puncturing device; and a second position, or delivery position, that is substantially turned 90° relative to said first position, the opposite holes that have been pierced in the operculum now being coaxial with said air-outlet channel, in said second position the lower end of the air-outlet channel being in communication with the top of the seat of the operculum, while the bottom of said seat is in communication with the air-inlet opening.

With the insufflator according to the invention, the operculum is punctured while the turnable member is in its first position, thus preventing the powder from falling out of the operculum while it is punctured due to the drag of the puncturing pins acting onto the powder that is contained in it.

The turnable member is then turned 90° to bring it into said second position, so that the opposite holes in the operculum are coaxial with the air-outlet channel. The seat of the operculum, and therefore the inside thereof (the operculum is now punctured), is in communication with the air-inlet opening and with the air-outlet channel.

Actually, a small amount of powder can come out of the lower hole of the operculum when the turnable member is turned 90° and brought into its second position. This amount of powder is however very small because in the mass of the powder particles over the lower hole of the operculum the "arch effect" is displayed. Therefore only those powder particles can come out which are below said "arch" or, more exactly, "dome" that is formed above said lower opening. The diameter of the holes will obviously be the narrowest possible consistent with the need of affording an air flow enough to remove the powder from the operculum. Therefore, the amount of powder that come out is in practice negligible and however much lower that the amount coming out when the operculum is punctured by vertically directed pins.

From the above it can be recognized how simple the insufflator according to the invention is to manufacture and use.

In particular, the turnable member containing the seat of the operculum can profitably have a circular shape and be fitted in a suitable circular cavity provided in the body of the insufflator. The various parts of the latter can all be made of a non-toxic heat-mouldable plastic material.

In the insufflator according to the invention, the air-inlet opening will be in communication with a conventional hand pump suitably consisting of a non-toxic elastomer container whose interior is in communication with the air-inlet opening. Said container is provided with a one-way or check valve for the intake of the external air.

A similar valve may be provided at the air-inlet opening, so that also the above mentioned small amount of powder is prevented to fall down into the elastomer container.

The body of the insufflator according to the invention can be suitably provided with an ejection device for ejecting the turnable member from said body so as to ease loading of an operculum into said seat provided in the turnable member. Said ejection device can simply consist of a pusher that can be operated from the outside, for example by means of a knob, said pusher acting onto the internal face of the turnable member. A finger pressure on said knob is enough to push out the turnable member and ease its removal.

The turnable member can in turn comprise a similar ejection device to eject the empty operculum from its seat.

The loading of the operculum can also be carried out without the need of making the turnable member detachable from the body of the insufflator. In fact it can be provided that the operculum be loaded when the turnable member is in a third position in which the seat of the operculum is coaxial with a radial loading opening provided in the body of the insufflator. The diameter of said opening is wide enough for the operculum to be inserted into its seat. In this case, the ejection of the empty operculum can be eased by providing an ejection device of the above mentioned type and suitable to radially eject the empty operculum through said loading opening after bringing the turnable member again into said third position.

The invention will be better understood from the following description of an illustrative, non-limiting embodiment thereof, taken in conjunction with the enclosed drawings in which:

FIG. 1 is a front view of the insufflator according to the invention provided with a protective cover;

FIG. 2 is a side view of the same insufflator;

FIG. 3 is a top view of the same insufflator;

FIG. 6 is a less enlarged cross-section taken along line VI—VI of FIG. 1.

Figure 4:
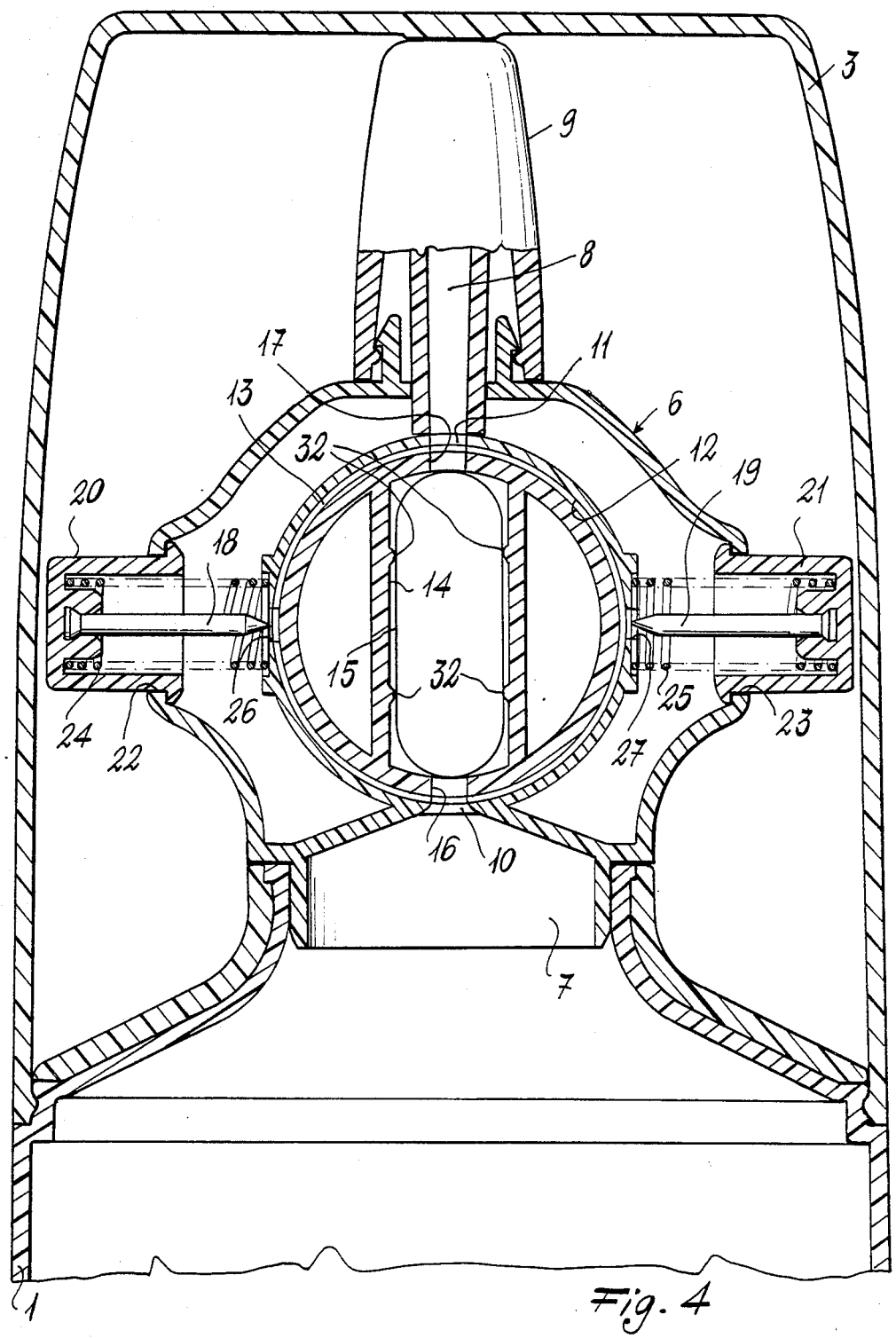
FIG. 4 is a partial enlarged cross-section taken along line IV—IV of FIG. 3.

From FIGS. 1, 2 and 3 the exterior appearance of the insufflator according to the invention can be seen. In particular, 1 is a container made of non-toxic elastomer that makes up the pump which can be hand-operated by pressing said container 1. The latter is provided with a one-way or check valve 2 that is sketched in the figures and allows the resilient container 1 to be filled with air after having been pressed. By pressing the resilient container 1 an air stream is generated that is needed for the operation of the insufflator.

From FIGS. 1, 2 and 3 the removable cover 3 that covers the body of the insufflator can also be seen. In said cover 3 there is provided a slit 4 from which a fin 5 projects whose function will be explained below.

Figure 5:
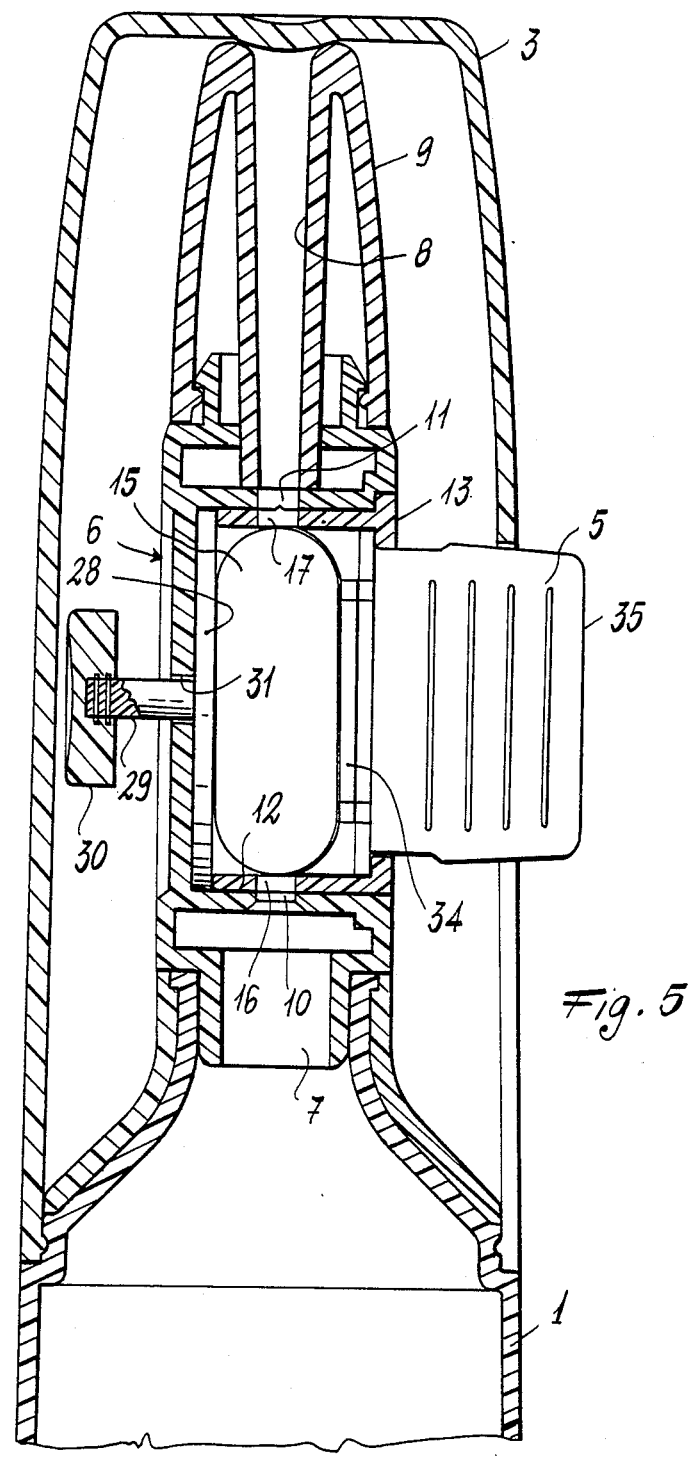
FIG. 5 is a partial, enlarged cross-section taken along line V—V of FIG. 1.

From FIGS. 4, 5 and 6 it can be seen how the insufflator is internally made. It comprises a body 6 having an air-inlet channel 7 communicating with the interior of the container 1. Body 6 also comprises an outlet channel 8 for the air that is charged with drug powder. In the illustrated embodiment the outlet channel 8 is provided with an adapter 9 having an anatomic shape in its upper part to allow the powder drug to be delivered through the nostrils.

Both the air-inlet channel 7 and the air-outlet channel 8 communicate respectively through openings 10, 11 with a central cylindrical cavity 12 (FIGS. 5 and 6) provided in body 6 and into which from outside a circular member 13 can be inserted that can turn within said cavity 12. The turnable member 13 has a diametral seat 14 in which the hard gelatine operculum 15 can be inserted. The operculum contains the drug in the form of a micronized powder. Seat 14 shows in axially opposite positions two holes 16, 17 respectively matching said openings 10 and 11 when said turnable member 13 is in the position shown in FIGS. 4, 5 and 6, that is in its socalled second position. In this way, when the turnable member 13 is in its second position, seat 14 is in communication with both the air-inlet channel 7, and therethrough with pump 1, and with the air-outlet channel 8.

The turnable member 13 can be rotated between two positions, namely the position we already called the second position and a position that is rotated 90° relative to said second position, and that we will refer to as first position. When the turnable member 13 is in its first position, holes 16, 17 are coaxial with two opposite pins 18, 19 secured to knobs 20, 21 respectively, which can be horizontally reciprocated through opposite slide openings 22, 23 provided in body 6. The knobs 20, 21 are provided with return springs 24, 25 respectively.

When the turnable member 13 is in its first position, by pressing knobs 20 and 21 inwardly pins 18, 19 pass through corresponding openings 26, 27 provided in the wall of cavity 12 and through said corresponding holes 16, 17 respectively, thus puncturing the operculum 15 previously inserted into its seat 14 at the top of both spherical caps of said operculum. Two opposite, substantially coaxial holes are thus provided in the operculum. After turning the turnable member 13 in its second position, said holes lay on the same axis as both holes 16 and 17 of the seat 14 and the corresponding openings 10 and 11 communicating with air-inlet 7 and outlet 8 channels respectively. A straight, vertical path for the air stream is thus obtained, said path being coaxial with the operculum 15.

On the bottom of the circular cavity 12 a plate pusher 28 is provided (FIGS. 5 and 6). Said pusher is secured to one end of a stem 29 that passes through an opening 31 provided in the back of body 6. The stem 29 has a knob 30 secured to the other end thereof.

The assembly consisting of plate 28, stem 29 and knob 30 makes up an ejection device for the easy removal of turnable member 13 from cavity 12. In fact, by pressing knob 30, the turnable member 13 will be pushed outside, thus easing its removal from body 6. With the turnable member 13 removed, an operculum 15 can be easily inserted into seat 14.

From FIGS. 4 and 6 it can be seen that seat 14 preferably has, on both side walls, some protrusions 32 by means of which operculum 15 can be maintained in its position into seat 14. The protrusions 32 cause operculum 15 to be inserted into said seat 14 with a small pressure. Thereby it is prevented from accidentally falling out during the loading of the insufflator.

The insufflator is also provided with a device for ejecting the operculum from the turnable member 13 (see FIGS. 5 and 6) after having been used. Said ejection device consists of a pusher 34 in form of a saddle placed on the bottom of the seat 14 (see FIGS. 6 and 5). The saddle 34 is connected with an external fin 5 protruding through a slit 36 provided in the outside face of the turnable member 13. Said fin is secured to the saddle 34. When turnable member 13 is ejected from circular cavity 12, it is possible to eject, in turn, the empty operculum 15 by means of a little pressure on the vertical edge 35 of fin 5. Fin 5 is also used both to rotate the turnable member 13 to bring it into the desired positions and as a grasping device for the turnable member 13.

As already mentioned, the insufflator according to the invention will be suitably made of a non-toxic heat-mouldable plastic material whilst the resilient container 1, that works as a pump, will be made of a non-toxic elastomer. Springs 24 and 25 and pins 18 and 19 will be made of a suitable non-toxic plastic material or metal.

Although the operation of the insufflator should be already evident from the above description and the enclosed Figures, it will be briefly described in the following for the sake of a better understanding.

The first step will obviously consist of taking off the protective cover 3. Next one will: pull out the turnable member 13 from cavity 12 of body 6; insert operculum 15 into its seat 14 in the turnable member 13; fit the turnable member 13 into cavity 12, meanwhile bringing the member 13, by means of fin 5, into its first position where holes 16 and 17 of turnable member 13 are coaxial with pins 18 and 19; push knobs 20, 21 to axially puncture operculum 15 at both ends thereof; bring, by means of fin 5, the turnable member 13 into its second position (that is, turn it 90°) thus bringing holes 16 and 17 to match openings 10 and 11 respectively; introduce adapter 9 into the concerned cavity (for example in a nostril) or place its outlet opening near the area to be treated; repeatedly press the resilient container 1; pull out again the turnable member 13; eject the empty operculum 15 by lightly pressing edge 35 of fin 5; insert the turnable member 13 into cavity 12; and put on again protective cover 3.

It can be recognized from the above that the insufflator according to the present invention has a quite simple structure and can be easily manufactured. It can also be used in simple and reliable way and does not give rise to the above-mentioned draw-backs of the prior art apparatuses.

What is claimed is:

1. Insufflator for the administering drugs which are in the form of a powder pre-dosed into opercola, the insufflator comprising a body having an air-inlet opening coaxial with a substantially vertical outlet channel for carrying inlet air mixed with the powder drug, and a device with opposite substantially horizontal reciprocating pins for puncturing an operculum, said operculum being placed in a seat having two axially opposite holes, and characterized in that the seat for the operculum is provided in a member that is turnable relative to said body, and in that said turnable member can take at least two different positions: a first position, or operculum puncturing position, where the operculum is axially puncturable by the two opposite, substantially horizontal reciprocating pins through said two axially opposite holes in the seat; and a second position, or delivery position, that is substantially turned 90° relative to said first position, in which one of said axially opposite holes is coaxial with said air-outlet channel, and the other one of said axially opposite holes is in communication with the air-inlet opening.

2. Insufflator as claimed in claim 1, characterized in that the turnable member is detachable from said body.

3. Insufflator as claimed in claim 2, characterized in that the turnable member is housed in a cylindrical cavity provided in said body and coaxial therewith.

4. Insufflator as claimed in claim 3, characterized in that on the bottom of the cylindrical cavity there is provided a pusher that can be reciprocated parallel to the axis of rotation of the turnable member and can be operated from outside the body to ease the separation of the turnable member from said body.

5. Insufflator as claimed in claims 2, characterized in that on the bottom of the operculum seat there is provided a pusher that can be reciprocated parallel to the axis of rotation of the turnable member and can be operated from outside said turnable member for the ejection of the empty operculum from its seat when the turnable member is separated from said body.

6. Insufflator as claimed in claim 5, characterized in that the turnable member is provided with an outwardly projecting fin to ease the turning of said turnable member.

7. Insufflator as claimed in claim 6, characterized in that said fin is secured to said pusher for the ejection of the operculum from its seat.

8. Insufflator as claimed in claim 1, characterized in that the turnable member can take a third position in which the seat of the operculum is coaxial with a radial loading opening that is provided in the body of the insufflator, the diameter of said loading opening being large enough to allow the insertion of the operculum into its seat.

9. Insufflator as claimed in claim 8, characterized in that in the body of the insufflator there is provided a pusher that can be reciprocated perpendicular to the axis of rotation of the turnable member and that can be operated from the outside of said body to ease the ejection of the empty operculum through said loading opening when the turnable member is in said third position.

10. Insufflator as claimed in claim 1, characterized in that a one-way or check valve is provided at the air-inlet opening to prevent the powder from falling down through said opening.

11. Insufflator as claimed in claim 1, characterized in that the turnable member is provided with an outwardly projecting fin to ease the turning of said turnable member.

* * * * *